(12) United States Patent
Masuko et al.

(10) Patent No.: US 6,659,289 B1
(45) Date of Patent: Dec. 9, 2003

(54) HEMOCATHARTIC COLUMN FOR PURIFYING BLOOD

(75) Inventors: Sanae Masuko, Shiga (JP); Tadayuki Matsumoto, Shiga (JP); Shinji Shimizu, Shiga (JP)

(73) Assignee: Toray Industries, Inc. (JP)

( * ) Notice: Subject to any disclaimer, the term of this patent is extended or adjusted under 35 U.S.C. 154(b) by 0 days.

(21) Appl. No.: 09/601,936

(22) PCT Filed: Dec. 20, 1999

(86) PCT No.: PCT/JP99/07145

§ 371 (c)(1),
(2), (4) Date: Aug. 10, 2000

(87) PCT Pub. No.: WO00/38763

PCT Pub. Date: Jul. 6, 2000

(30) Foreign Application Priority Data

Dec. 24, 1998 (JP) ............................................. 10/367939

(51) Int. Cl.⁷ ............................................. B01D 29/00
(52) U.S. Cl. ........................ 210/435; 210/437; 210/457; 210/459; 210/460; 210/503; 210/505
(58) Field of Search ................................. 210/353, 435, 210/437, 459, 460, 456, 457, 503, 504, 505, 506, 508

(56) References Cited

FOREIGN PATENT DOCUMENTS

| JP | 60-13481 | * | 4/1985 |
| JP | 8-164202 | * | 6/1996 |
| JP | 9-239022 | * | 9/1997 |
| JP | 63-53826 | * | 10/1998 |
| JP | 2853452 | * | 11/1998 |

* cited by examiner

*Primary Examiner*—John Kim
(74) *Attorney, Agent, or Firm*—Piper Rudnick LLP

(57) ABSTRACT

A hemocathartic column and apparatus, in which a column containing an adsorber capable of adsorbing and removing impurity components in blood, and in which the blood of an organism is extracorporeally circulated through the column, to be purified, and further in which if the pressure of blood at 120 minutes after start of blood circulation is $P_{120}$ and the pressure of blood at 5 minutes after start of blood circulation is $P_5$, then a relation of $(P_{120}/P_5) \leq 1.3$ is satisfied.

5 Claims, 2 Drawing Sheets

HEMOCATHARTIC COLUMN FOR PURIFYING BLOOD

TECHNICAL FIELD

This invention relates to a hemocathartic method and a hemocathartic column. Particularly it relates to a hemocathartic column, comprising a column containing an adsorber capable of adsorbing and removing impurity components in the blood, a blood introducing duct connected with the inlet of the column, and a blood delivering duct connected with the outlet of the column, whereby the inlet of the blood introducing duct and the outlet of the blood delivering duct are connected with blood vessels of an organism, to be used in a blood circulation system (extracorporeal circulation system) in which the blood delivered from the organism flows through the blood introducing duct into the column, has the impurity components in the blood removed by the adsorber in the column, goes out of the column, and flows through the blood delivery duct, to be reintroduced in the organism. This invention also relates to a hemocathartic method using the column.

BACKGROUND ART

One of hemocathartic therapeutic methods is extracorporeal circulation therapy. This extracorporeal circulation therapy has been actively practiced since the time when the hemodialysis of acute renal failure began to be clinically applied. So, various techniques have been developed, and some are already clinically applied. The extracorporeal circulation therapy attracts attention since it allows therapy which cannot be effected by medicines.

As a column used for the extracorporeal circulation therapy, a column for extracorporeal circulation, comprising a cylinder, a first end plate provided at one end of the cylinder, a second end plate provided at the other end of the cylinder, a blood flow pipe opened at one end, closed at the other end, extending through the central portion of the first end plate into the cylinder and having many blood-flowing openings in the circumferential surface in the portion located in the cylinder, and an adsorber positioned between the outer circumferential surface of the blood flow pipe and the inner circumferential surface of the cylinder, wherein a blood-flowing clearance is formed between the inner circumferential surface of the cylinder and the outer circumferential surface of the second end plate, is described in Japanese Patent Laid-Open (Kokai) No. 1997-239022.

When this publicly known column for extracorporeal circulation was used for hemocatharsis, it was found that the pressure of the blood flowing in the blood introducing duct connected at one end with a blood vessel of an organism and connected at the other end with the openings of the blood flow pipe rose with the lapse of time. The pressure rise is likely to damage the thrombocytes and other blood components in the extracorporeally circulated blood.

DISCLOSURE OF THE INVENTION

This invention solves the problem of blood pressure rise during blood treatment incidental to the prior art, by presenting a hemocathartic method and a hemocathartic column which does not require the blood treatment by extracorporeal circulation to be discontinued in the middle of treatment.

The hemocathartic method of this invention to solve the above problem is as described below.

A hemocathartic method performed by use of a column comprising a cylinder, a first header closing one end of the cylinder and having a first blood passage communicating into the cylinder, a second header closing the other end of the cylinder and having a second blood passage communicating into the cylinder, and an adsorber contained in the cylinder, wherein a relation of $(P_{120}/P_5) \leq 1.3$ is satisfied, where $P_{120}$ is the pressure of the blood at 120 minutes after start of blood supply in the first blood passage when the blood to be purified is supplied from the first blood passage or in the second blood passage when the blood is supplied from the second blood passage, and $P_5$ is the pressure of blood at 5 minutes after start of such blood supply in the corresponding blood passage.

In the column of this invention, it is preferable that a first end plate is provided at the end of the cylinder on the first header side, that a second end plate is provided at the end of the cylinder on the second header side, that a blood flow pipe extending from the first end plate to the second end plate and provided with a circumferential surface having many blood-flowing openings is provided in the central portion of the cylinder, that the blood flow pipe communicates at one end with the first header and is closed at the other end, that no clearance is formed between the outer circumferential surface of the first end plate and the inner circumferential surface of the cylinder, that a blood-flowing clearance is formed between the outer circumferential surface of the second end plate and the inner circumferential surface of the cylinder, that the adsorber is contained between the inner circumferential surface of the cylinder and the outer circumferential face of the blood flow pipe, and that the linear velocity LV (cm/min) of the blood flow through the many openings of the blood flow pipe satisfies a relation of $3 \text{ cm/min} \leq LV \leq 16 \text{ cm/min}$.

In this invention, it is preferable that the adsorber is an aggregate of fibers or grains. An aggregate of fibers is more preferable.

In this invention, it is preferable that the adsorber carries a bioactive substance.

The hemocathartic column of this invention to solve the problem is as follows.

A hemocathartic column comprising a cylinder, a first header closing one end of the cylinder and having a first blood passage communicating into the cylinder, a second header closing the other end of the cylinder and having a second blood passage communicating into the cylinder, and an adsorber contained in the cylinder, wherein a first end plate is provided at the end of the cylinder on the first header side; a second end plate is provided at the end of the cylinder on the second header side; a blood flow pipe extending from the first end plate to the second end plate and provided with many blood-flowing openings in the circumference surface is provided in the central portion of the cylinder; the blood flow pipe communicates at one end to the first header and is closed at the other end; no clearance is formed between the outer circumferential surface of the first end plate and the inner circumferential surface of the cylinder; a blood-flowing clearance is formed between the outer circumferential surface of the second end plate and the inner circumferential surface of the cylinder; the adsorber is contained between the inner circumferential surface of the cylinder and the outer circumferential surface of the blood flow pipe; and the opening rate OR (%) which refers to the rate of the total opening area TOA of the many openings provided in the circumferential surface of the blood flow pipe to the surface area SA of the portion of the blood flow pipe facing the adsorber satisfies a relation of $15\% \leq OR \leq 85\%$.

If the opening rate OR (%) is more than 85% or less than 15%, the value of ($P_{120}/P_5$) is more than 1.3. It is preferable that the opening rate OR (%) satisfies a relation of 35%≦OR≦65%. In this case the value of ($P_{120}/P_5$) is 1.2 or less.

In this invention, it is preferable that the adsorber is an aggregate of either fibers or grains. An aggregate of fibers is more preferable.

In this invention, it is preferable that the adsorber carries a bioactive substance.

THE BEST MODE FOR CARRYING OUT THE INVENTION

Figure 1:
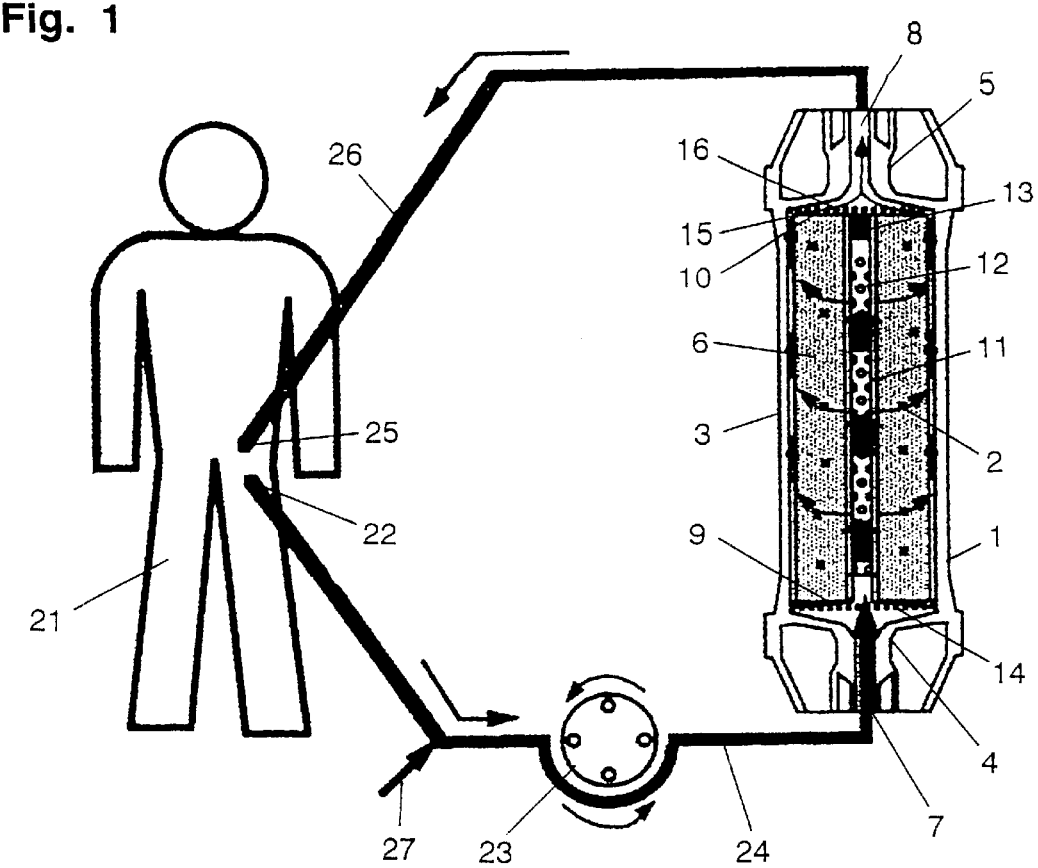
FIG. 1 is a conceptual drawing for illustrating a state where hemocathartic therapy is performed using the hemocathartic column of this invention.

In FIG. 1, the hemocathartic column 1 of this invention (shown as a vertical sectional view, in which the inside blood flow is indicated by arrows 2) consists of a cylinder 3, a first header 4 for closing one end of the cylinder 3, a second header 5 for closing the other end of the cylinder 3, and an adsorber 6 contained in the cylinder 3, and the first header 4 and the second header 5 are provided with a first blood passage 7 and a second blood passage 8 respectively communicating into the cylinder 3.

In the column 1 shown in FIG. 1, a first end plate 9 and a second end plate 10 are respectively provided at both the ends of the adsorber 6 in the axial direction of the cylinder 3, and a blood flow pipe 11 extending from the first end plate 9 to the second end plate 10 is located in the central portion of the cylinder 3.

The blood flow pipe 11 has many blood-flowing openings 12 in the outer circumferential face thereof, and is opened at one end outside the first end plate 9, to communicate to the first blood passage 7, being closed at the other end by a closure 13.

The first end plate 9 is installed in the cylinder 3, with the outer circumferential surface of the first end plate 9 fitted in the inner circumferential surface of the cylinder 3. On the outside surface of the first end plate 9, a filter 14 is installed. The blood flowing into the cylinder 3 from the first blood passage 7 passes through the filter 14 and flows into the blood flow pipe 11.

The second end plate 10 is installed in the cylinder 3, with a blood-flowing clearance 15 formed between the outer circumferential surface of the second end plate 10 and the inner circumferential surface of the cylinder 3. The clearance 15 communicates to the second blood passage 8. On the outside surface of the second end plate 10, a filter 16 is installed. The blood which passes through the many openings 12 of the blood flow pipe 11 and flows into the space in the adsorber 6 flows through the adsorber 6 in the outer circumferential direction thereof, and during this flow, the impurity components are adsorbed and removed by the adsorber 6. The blood further flows through the clearance formed between the outer circumferential surface of the adsorber and the inner circumferential surface of the cylinder 3 and further through the filter 16, to reach the second blood passage 8.

As for the blood circulation through the column 1, the blood can be supplied into the cylinder 3 from the first blood passage 7 as described above, or on the contrary, can be supplied into the cylinder 3 from the second blood passage 8.

The column 1 shown in FIG. 1 has the blood flow pipe 11, being of radial flow type in which blood flows radially in the cylinder 3. However, a column using blood-flowable perforated plates as the first end plate 9 and the second end plate 10 can also be used. In this case, the blood flow pipe 11 is not necessary, and the column is of axial flow type in which blood flows in the axial direction.

In the hemocatharsis by extracorporeal circulation of blood using the column 1, a blood delivering duct 24 provided with a blood pump 23 and connected to a femoral vein 22 of a patient is connected to the first blood passage 7, and a blood return duct 26 connected to a femoral vein 25 of the patient 21 is connected to the second blood passage 8 for actuation by the blood pump 23. In this case, at the position indicated by arrow 27 upstream of the blood pump 23, an anticoagulant is supplied into the blood delivering duct 24.

Figure 2:
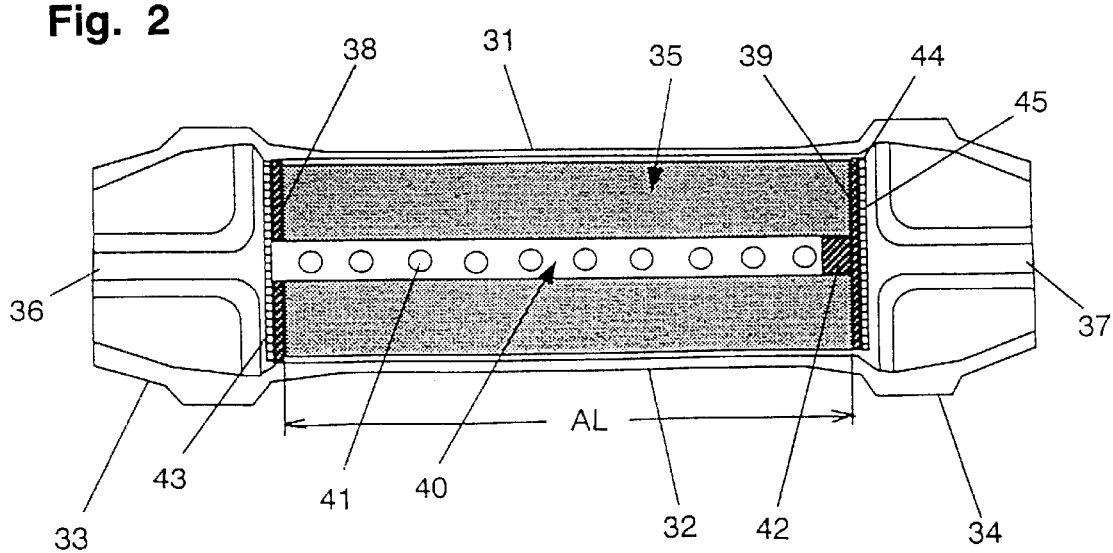
FIG. 2 is a longitudinal sectional view showing an embodiment of the hemocathartic column of this invention.

A longitudinal sectional view showing an embodiment of the hemocathartic column of this invention is shown in FIG. 2. In FIG. 2, the hemocathartic column 31 of this invention consists of a cylinder 32, a first header 33 closing one end of the cylinder 32, a second header 34 closing the other end of the cylinder 32, and an adsorber 35 contained in the cylinder 32, and the first header 33 and the second header 34 are provided with a first blood passage 36 and a second blood passage 37 respectively communicating into the cylinder 32.

At both the ends of the adsorber 35 in the axial direction of the cylinder 32, a first end plate 38 and a second end plate 39 are provided respectively, and a blood flow pipe 40 extending from the first end plate 38 to the second end plate 39 is located at the central portion of the cylinder 32.

The blood flow pipe 40 has many blood-flowing openings 41 in the outer circumferential surface thereof, and is opened at one end outside the first end plate 38, to communicate to the first blood passage 36, being closed at the other end by a closure 42.

The first end plate 38 is installed in the cylinder 32, with the outer circumference of the first end plate 38 fitted in the inner circumferential surface of the cylinder 32. On the outside surface of the first end plate 38, a filter 43 is installed. The blood flowing into the cylinder 32 from the first blood passage 36 flows through the filter 43 into the blood flow pipe 40.

The second end plate 39 is installed in the cylinder 32, with a clearance 44 formed between the outer circumferential surface of the second end plate 39 and the inner circumferential surface of the cylinder 32. The clearance 44 communicates to the second blood passage 37. On the outside surface of the second end plate 39, a filter 45 is installed. The blood which passes through the many openings 41 of the blood flow pipe 40 and flows into the space in the adsorber 35 flows through the adsorber 35 in the outer circumferential direction thereof, and in this state, the impurity components are adsorbed and removed by the adsorber 35. The blood further flows through the clearance formed between the outer circumferential surface of the adsorber 35 and the inner circumferential surface of the cylinder 32 and further through the filter 45, to reach the second blood passage 37.

In the blood circulation through the column 31, blood can be supplied into the cylinder 32 from the first blood passage 36 as described above, or on the contrary, blood can be supplied into the cylinder 32 from the second blood passage 37.

If the surface area of the portion of the blood flow pipe 40 facing the adsorber 35 is SA, the length of the portion of the blood flow pipe 40 in the axial direction facing the adsorber 35 is AL and the outer circumference length of the blood flow pipe 40 is OPL, then there is a relation of SA=AL× OPL. If the opening rate of the blood flow pipe 40 is OR (%) and the total opening area of the many openings 41 is TOA, then the opening rate OR (%) can be obtained from OR= (TOA/SA)×100%.

The opening rate OR of the blood flow pipe 40 in the hemocathartic column of this invention is 15%≦OR≦85%. A preferable range is 35%≦OR≦65%.

It is preferable that the adsorber 35 is an aggregate of grains or fibers. It is preferable that the fibrous aggregate is a knitted fabric, woven fabric or nonwoven fabric.

It is preferable that the grains or fibers have a surface area of 0.1 to 100 m$^2$/g. This surface area is measured according to the BET method. In this invention, this measurement was effected by using a high precision full automatic gas adsorber (BELSORP 36 produced by Nippon Bell).

It is preferable that the fibbers are polystyrene fibers, crosslinked polystyrene fibers, acrylic acid acrylonitrile copolymer fibers or polyvinyl alcohol fibers having carboxyl groups. The reason is that functional groups can be easily introduced. In view of processability and durability, so-called islands-in-sea type yarns reinforced by an island component can be preferably used. In this case, islands-in-sea type yarns using polystyrene as the sea component and polypropylene as the island component can be preferably used.

The adsorber 35 can carry a bioactive substance. The bioactive substances which can be used here include polypeptides such as polymyxin B, vancomycin, actinomycin and Viomycin.

Fibers having a bioactive substance immobilized can be produced by mixing fibers with functional groups and a bioactive substance, or by adding a peptide condensing agent. The peptide condensing agent can be {cyclohexylcarbodiimide, 1-ethyl-3-(3-dimethylaminopropyl)-carbodiimide}.

If the adsorber 35 is formed by a knitted fabric or woven fabric of fibers, the knitted fabric or woven fabric can be wound around the blood flow pipe 40 in layers up to a desired thickness. The assembled adsorber 35 which is provided, at one end, with the first end plate 38 having the filter 43 attached and, at the other end, with the second end plate 44 having the filter 45 attached is inserted into and fixed in the cylinder 32. Then, at both the ends of the cylinder, the first header 33 and the second header 34 are attached and fixed.

Figure 3:
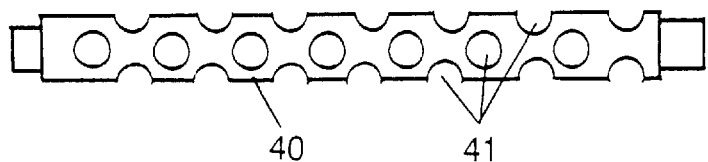
FIG. 3 is a front view showing an example of the blood flow pipe used in the hemocathartic column of this invention.

The detail of the blood flow pipe 40 is shown in FIG. 3. The many openings 41 are circular. Other modes of the many openings provided in the outer circumferential surface of the blood flow pipe include many openings 41a formed as slits in the blood flow pipe 40a shown in FIG. 4 and many openings 41b formed as meshes in the blood flow pipe 40b shown in FIG. 5.

The measurement of blood pressure in the first blood passage or second blood passage in this invention is effected based on the following definition.

Figure 6:
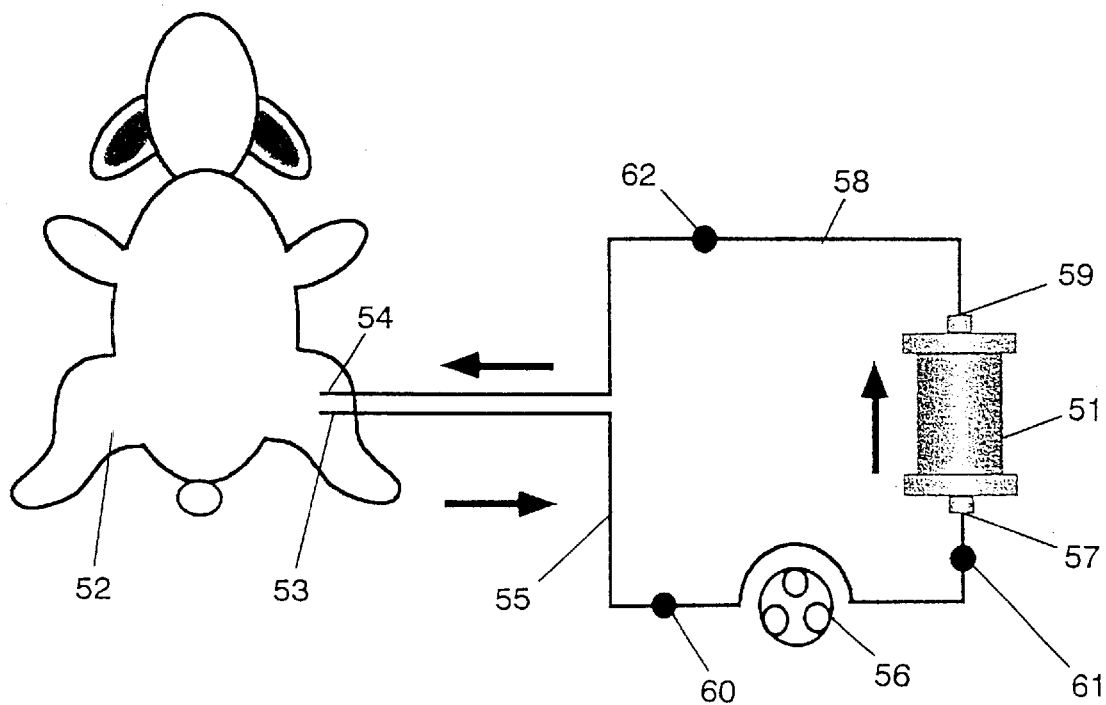
FIG. 6 is a conceptual view for illustrating a state where the performance of the hemocathartic column of this invention is tested.

The temporal change in the pressure of the blood circulated in the column is considered to be affected by the activity of blood components such as thrombocytes. So, a model material accurately reproducing the blood conditions in the organism should be circulated through the column 1, to measure the temporal change of pressure. However, there is no such appropriate model substance today. Therefore, the temporal change of pressure is measured by extracorporeally circulating blood of a rabbit. The mode of measurement is shown in FIG. 6.

The structure of the column 51 used for measurement is the same as that of the column 31 explained in FIG. 2, but the size (volume) should be such as to allow the extracorporeal circulation of a rabbit. Specifically the evaluation column 51 used has a form similar to that of the column 1 used for evaluation of a human but is reduced to ¹⁄₁₅ in volume. The packing rate of the adsorber (not illustrated) in the evaluation column 51 is the same as that of the adsorber 6 of the column 1.

The evaluation column 51 is washed with 500 ml of physiological salt solution. Then, 100 ml of physiological salt solution containing 1000 U of heparin is primed.

The rabbit 52 used is a New Zealand White male rabbit with a body weight of 2.5 to 3.5 kg and a hematocrit of 40% or more and having 30×10$^4$/µl or more thrombocytes.

Into an inguinal femoral artery and an inguinal femoral vein of the rabbit 52, 18G indwelling needles 53 and 54 are inserted. A first blood circuit 55 is connected, at one end, with the indwelling needle 53, and, at the other end, with a blood introducing port 57 of the evaluation column 51 via a peristaltic pump 56 for liquid feed (produced by Iwaki). A second blood circuit 58 is connected, at one end, with the indwelling needle 54, and, at the other end, with a blood delivering port 59 of the evaluation column 51. The blood circuit 55 is provided with a first air trap 60 upstream of the pump 56 and with a second air trap 61 downstream. The blood circuit 58 is provided with a third air trap 62.

The blood circuits 55 and 58 are human blood circuits with an inner diameter of 3 mm (AP Chambers produced by Nipro). The blood flow rate in the blood circuits 55 and 58 is 20 ml/min. The blood flowing through the evaluation column 51 is returned to the inguinal femoral vein from the indwelling needle 54.

In extracorporeal circulation, to prevent blood coagulation, 100 U/kg of heparin is shot from the air trap 60 as soon as blood begins to flow, and during extracorporeal circulation, 60 U/kg/hr of heparin is shot continuously from the air trap 60. For the continuous injection, a syringe pump (produced by Thermo) (not illustrated) is used in this invention.

For measuring the pressure of blood at the inlet to the evaluation column 51, the tube connected to the injection needle inserted into the blood circuit 55 from the air trap 61 is connected to a pressure measuring instrument. After start of circulation, the pressure change is monitored, and the results are recorded on a chart. From the measured pressure values $P_5$ and $P_{120}$ at 5 minutes and 120 minutes after start of circulation, the value of $P_{120}/P_5$ is obtained as the pressure rise value.

For the measurement of the pressure rise value, identical five new evaluation columns and five rabbits defined above are used. Of the obtained five pressure rise values, the larger three values are averaged to be adopted as the pressure rise value.

EXAMPLES

Example 1

As fibers constituting the adsorber 35, islands-in-sea type conjugate yarns were used. The island component was polypropylene (Mitsui "Nobrene" J3HG) and the sea component was a mixture consisting of 46 parts by weight of polystyrene ("Styron" 666) and 4 parts by weight of polypropylene (Sunitomo "Nobrene" WF-727-F). The island component rate in the fibers was 50 parts by weight. One filament had 16 islands, a fineness of 2.6 deniers, a tensile strength of 2.9 g/d and an elongation of 50%. Each of the yarns constituting the adsorber 35 consisted of 42 such filaments.

Fifty grams of the fibers were immersed in a mixed solution consisting of 113 g of N-methylol-α-chloroacetamide, 750 g of nitrobenzene, 7500 of 98% sulfuric acid and 1.61 g of paraformaldehyde, for reaction treatment at 10° C. for 2 hours.

The fibers were taken out of the reaction solution, washed with 1,300 g of nitrobenzene, then washed with 1,000 ml of water and neutralized by 31.3 ml of 25% NaOH solution. The obtained fibers were washed with 1,250 ml of methanol and then with hot water, to obtain chloroacetamidomethylated fibers.

The obtained chloroacetamidomethylated fibers were immersed in a solution with 1.25 g of polymyxin B (produced by DUMEX) dissolved in 800 ml of water and further containing 31.1 ml of 0.1N NaOH, and the mixture was shaken for 1 hour. Thus, polymyxin B was immobilized in the fibers by reaction. The obtained fibers were washed with 800 ml of 0.077N hydrochloric acid three times, and then washed with 800 ml of water three times, to obtain polymyxin B immobilized fibers. The amount of polymyxin B immobilized in the fibers was measured by an amino acid analysis method, and found to be 6 mg/g.

The volume of the evaluation column 51 was set at 1/15 of the volume of the human column 1, considering the weight of the rabbit. The external structure of the evaluation column 51 was made of polypropylene. The cylinder 32 had an inner diameter of 16.26 mm and a length of 50.81 mm. The blood flow pipe 40 had an inner diameter of 2.44 mm and a length of 50.00 mm. The outer circumferential surface of the blood flow pipe 40 had 28 circular openings 41 formed. The opening rate OR was 42.4%.

A knitted fabric produced from the polymyxin B immobilized fibers obtained in the above was wound around the outer circumferential surface of the blood flow pipe 40 like a roll, to form the adsorber 35. The total weight of the wound knitted fabric was 3.7 g. At both the ends of the adsorber 35, the first end plate 38 having the filter 43 attached and the second end plate 39 having the filter 45 attached were installed respectively. The assembled adsorber 35 was inserted into and fixed in the cylinder 32. At both the ends of the cylinder 35, the first header 33 and the second header 34 were respectively installed, to prepare the evaluation column 31.

The column 31 was washed with water or an aqueous solution harmless to the human body such as physiological salt solution and sterilized by high pressure steam, to produce an evaluation column 31 for extracorporeal circulation.

The column 31 was washed with 500 ml of physiological salt solution and primed by 100 ml of physiological salt solution containing 1000 U of heparin. The column 31 was used for treating the blood of a New Zealand White male rabbit with a weight of 2.5 to 3.5 kg for extracorporeal circulation. The rabbit was anesthetized by Nembutal.

The blood treatment conditions by extracorporeal circulation and the measurement of the pressure rise value of blood after start of treatment were effected as described above. The extracorporeal circulation was continued for 2 hours.

The measured values of blood pressure at 5 minutes and 120 minutes after start of treatment, and the pressure rise value are shown in Table 1. The linear velocity LV of blood flow at the openings 41 was calculated as 5.7 cm/min.

Comparative Example

Extracorporeal circulation was effected as described for Example 1, except that the opening rate OR of the blood flow pipe 40 of the column 31 used in Example 1 was changed to 10.6% in the column used in this comparative example. The measured values of blood pressure at 5 minutes and 120 minutes after start of treatment, and the pressure rise value are shown in Table 1. The linear velocity LV of the blood flow at the openings 41 was calculated as 22.7 cm/min.

Example 2

Figure 4:
FIG. 4 is a front view showing another example of the blood flow pipe.
Figure 5:
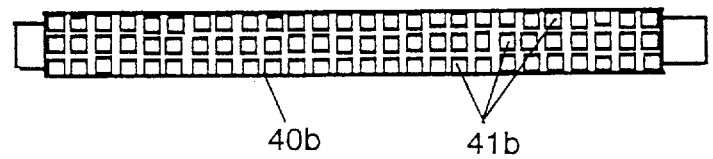
FIG. 5 is a front view showing a further other example of the blood flow pipe.

Extracorporeal circulation treatment was effected as described for Example 1, except that the blood flow pipe 40 in the evaluation column 31 prepared in Example 1 was replaced by the blood flow pipe 40a having slits 41a shown in FIG. 4, in the evaluation column. The number of slits 41 was 4, and the opening rate OR was 42.4%.

The measured values of blood pressure at 5 minutes and 120 minutes after start of treatment, and the pressure rise value are shown in Table 1. The linear velocity LV of blood flow at the openings 41a was calculated as 5.7 cm/min.

TABLE 1

|  | Inlet pressure (mmHg) | | |
| --- | --- | --- | --- |
|  | 5 minutes later | 120 minutes later | Pressure rise value |
| Example 1 | 43.7 | 41.0 | 0.94 |
| Comparative Example 1 | 34.0 | 89.3 | 2.41 |
| Example 2 | 53.0 | 35.5 | 0.67 |

Industrial Applicability

This invention presents a hemocathartic method and apparatus which allow hemocatharsis in a state in which blood components are unlikely to be damaged during circulatory hemocatharsis, since the pressure rise of blood is inhibited during hemocatharsis by extracorporeal circulation.

What is claimed is:

1. A hemocathartic column comprising a cylinder, a first header closing one end of the cylinder and having a first blood passage communicating into the cylinder, a second header closing the other end of the cylinder and having a second blood passage communicating into the cylinder, and an adsorber contained in the cylinder, wherein a first end plate is provided at the end of the cylinder on the first header side; a second end plate is provided at the end of the cylinder on the second header side; a blood flow pipe extending from the first end plate to the second end plate and provided with many blood-flowing openings in the circumference surface is provided in the central portion of the cylinder; the blood flow pipe communicates, at one end, to the first header and is closed at the other end; no clearance is formed between the outer circumferential surface of the first end plate and the inner circumferential surface of the cylinder; a blood-flowing clearance is formed between the outer circumferential surface of the second end plate and the inner circumferential surface of the cylinder; the adsorber is contained between the inner circumferential surface of the cylinder and the outer circumferential surface of the blood flow pipe; and the opening rate OR (%) which refers to the rate of the total opening area TOA of the many openings provided in the circumferential surface of the blood flow pipe to the surface area SA of the portion of the blood flow pipe facing the adsorber satisfies a relation of $15\% \leq OR \leq 85\%$.

2. A hemocathartic column according to claim 1, wherein the opening rate OR (%) satisfies a relation of $35\% \leq OR \leq 65\%$.

3. A hemocathartic column according to claim 1 or 2, wherein the adsorber is an aggregate of fibers or grains.

4. A hemocathartic column according to claim 3, wherein the adsorber is an aggregate of fibers.

5. A hemocathartic column according to claim 3, wherein the adsorber carries a bioactive substance.

* * * * *